United States Patent [19]

King et al.

[11] Patent Number: 5,693,816
[45] Date of Patent: Dec. 2, 1997

[54] PROCESS FOR THE PREPARATION OF DIISOPINOCAMPHEYLCHLOROBORANE

[75] Inventors: Anthony On-Ping King, Hillsborough; Robert D. Larsen, Bridgewater; Thomas R. Verhoeven, Cranford; Mangzhu Zhao, Edison, all of N.J.

[73] Assignee: Merck & Co., Inc., Rahway, N.J.

[21] Appl. No.: 586,037

[22] Filed: Jan. 16, 1996

Related U.S. Application Data

[62] Division of Ser. No. 289,077, Aug. 11, 1994, Pat. No. 5,545,758.

[51] Int. Cl.⁶ .................................................. C07D 215/14
[52] U.S. Cl. ............................................................. 546/174
[58] Field of Search ................................................ 546/174

[56] References Cited

U.S. PATENT DOCUMENTS 5,043,479  8/1991  Brown .
5,270,324  12/1993  Zamboni et al. ................. 546/174
5,292,946  3/1994  Simpson et al. .

OTHER PUBLICATIONS

J. Am. Chem. Soc., 1983, 105, 2092–2093, Brown, et al.
J. Am. Chem. Soc., 1972, 94, 2112–2113, Brown, H.C. and Ravindran, N.
J. Org. Chem., 1987, 52, 5406 Brown, et al.
J. Org. Chem., 1986, 51, 3394, Brown, H.C., et al.
J. Org. Chem., 1988, 53, 2916, Srebnik, et al.
J. Am. Chem., Soc., 1988, 1539–1546, vol. 110, Brown, et al.
J. Org. Chem., 1993, 58, 3731–3735, King, et al.

*Primary Examiner*—James H. Reamer
*Attorney, Agent, or Firm*—Mollie M. Yang; David L. Rose

[57] ABSTRACT

The present invention relates to an improved process for the in situ preparation of diisopinocampheylchloroborane which comprises reacting sodium borohydride and boron trichloride with α-pinene. The diisopinocampheylchloroborane thus obtained may be used, without isolation, to reduce prochiral ketones to their corresponding alcohols in high optical purity.

3 Claims, No Drawings

PROCESS FOR THE PREPARATION OF DIISOPINOCAMPHEYLCHLOROBORANE

This is a division of application Ser. No. 08/289,077 filed Aug. 11, 1994 now U.S. Pat. No. 5,545,758.

BACKGROUND OF THE INVENTION

The invention concerns the preparation of diisopinocampheylchloroborane. The invention also relates to the use of a crude diisopinocampheylchloroborane product in the reduction of prochiral ketones.

Diisopinocampheylchloroborane is a well known chiral reducing agent, and several methods for its preparation have been reported. In one early reference (Brown, H. C. and Jadhav, P. K., *J. Am. Chem. Soc.*, 1983, 105, 2092–2093), diisopinocampheylchloroborane was prepared by reacting monochloroborane etherate with α-pinene in diethyl ether. The monochloroborane etherate was in turn prepared from lithium borohydride and boron trichloride (Brown, H. C. and Ravindran N., *J. Am. Chem. Soc.*, 1972, 94, 2112–3). U.S. Pat. No. 5,043,479 reported that the above process produced a product mixture which was unsatisfactory for achieving asymmetric reduction of ketones in high enantiomeric excess.

U.S. Pat. No. 5,043,479 further reported a novel method for the preparation of diisopinocampheylchloroborane. In this process, the intermediate diisopinocampheylborane must first be prepared and isolated by crystallization. This intermediate is highly sensitive to both oxygen and water, thus complicating its isolation. The enantiomeric purity of diisopinocampheylchloroborane was increased to >99% after crystallization, starting from α-pinene of an optical purity of approximately 90%. This upgrading of the enantiomeric purity of diisopinocampheylchloroborane via crystallization was deemed critical for obtaining maximum enantioselectivity in the reduction of ketones to alcohols. See Brown, H. C. et al, *J. Org. Chem.*, 1987, 52, 5406 and references therein; Brown, H. C. et al, *J. Org. Chem.*, 1986, 51, 3394; Srebnik, M. et at, *J. Org. Chem.* 1988, 53, 2916; and Brown, H. C. et al, *J. Am. Chem. Soc.*, 1988, 1539.

In U.S. Pat. No. 5,292,946 it was reported that diisopinocampheylchloroborane prepared in-situ, without isolation or discrete purification of either the final product or the intermediate diisopinocampheylborane, performs in an equal manner to the isolated reagent. The processes in U.S. Pat. No. 5,043,479 and 5,292,946 both require the use of the corrosive reagent hydrogen chloride, and are therefore less than ideal for industrial application.

In yet another process (King, A. O. et al, *J. Org. Chem.*, 1993, 58, 3731–5), diisopinocampheylchloroborane was prepared from monochloroborane-dimethylsulfide complex and α-pinene. The boron source in this process contains the stench compound dimethylsulfide, making it an undesirable reagent to use in large amounts.

The prior reported processes all require the use of either borane or monochloroborane, both of which are expensive reagents and both are very sensitive to oxygen and moisture. Therefore, there exists the need for an economical, convenient and efficient method for the preparation of a diisopinocampheylchloroborane product suitable for the reduction of prochiral ketone to give hydroxy compounds with high optical purity.

SUMMARY OF THE INVENTION

The present invention is directed to in-situ preparation of diisopinocampheylchloroborane, and the use of same in the reduction of prochiral ketones to alcohols with high optical purity.

DETAILED DESCRIPTION OF THE INVENTION

The present invention provides a process for the preparation of diisopinocampheylchloroborane which comprises: contacting sodium borohydride and α-pinene with boron trichloride, in an inert organic solvent to provide a composition containing diisopinocampheylchloroborane.

In a preferred embodiment the α-pinene is (1R)-(+)-α-pinene, and the diisopinocampheylchloroborane has the formula I:

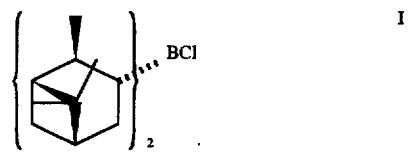

As used herein, "a composition containing diisopinocampheylchloroborane" is intended to indicate that the named reaction product diisopinocampheylchloroborane is not in any manner or degree isolated from such materials as the solvent, unreacted reagents, or possible side reaction products, that may be present in the reaction vessel. The abbreviation "ee" stands for enantiomeric excess. The term "high optical purity" means at least a 95: 5 ratio of the enantiomeric pair favoring the desired enantiomer.

The α-pinene used in the present process may be the (1R)-(+)- or the (1S)-(−)-α-pinene in which the enantiomeric excess may be as low as about 70%. Thus, even α-pinene with optical purity of about 70% routinely results in about 94% optically pure final alcohol. α-Pinene of optical purity lower than about 70% may also be used with slight sacrifice of optical purity of the final alcohol. In a preferred embodiment, (1R)-(+)-α-pinene with 70% or higher ee is used.

The organic solvent used in the present process may be any that does not substantially interfere with the desired reaction. Preferred solvents are polyoxygenated ethers. Examples of polyoxygenated ether include, but are not limited to, 1,2-dimethoxyethane, diglyme, triglyme, and the like. A preferred polyoxygenated solvent is 1,2-dimethoxyethane.

The reaction may be carried out at temperature from about −40° C. to about 60° C. Preferably, the temperature of the reaction mixture is maintained at about 0° C. or lower while boron trichloride is being added to the other reactants; subsequently, the temperature may be raised up to about 40° C. The reaction is allowed to proceed until substantially complete which may be from about 15 min. to about 2 hours; typically the reaction is essentially complete with about 30 min. The progress of the reaction may be monitored by methods known in the art; for example the consumption of α-pinene may be monitored by HPLC, or by determining the ratio of isopinocampheol (obtained by hydrogen peroxide oxidation of diisopinocampheylchloroborane) to α-pinene using gas chromatographic assay.

The reaction is preferably conducted under inert atmosphere, for example under nitrogen.

The molar ratio of sodium borohydride to boron trichloride is preferably about 1:1.1. The molar ratio of α-pinene to sodium borohydride and to boron trichloride is at least 4: 1: 1.1.

The composition containing diisopinocampheylchloroborane produced in the above process may be used without further purification to effect chiral reduction of prochiral ketones.

3

Accordingly, another aspect of the present invention provides a process for reducing a prochiral ketone to produce an optically active alcohol of high optical purity which comprises:

(a) contacting sodium borohydride and boron trichloride with α-pinene having optical purity of about 70% or higher, in an inert organic solvent to provide a composition containing diisopinocampheylchloroborane;

(b) reacting a prochiral ketone with the composition obtained in (a) to provide the corresponding optically active alcohol of high optical purity.

In a preferred embodiment, said α-pinene is (1R)(+) α-pinene, said diisopinocampheylchloroborane has the formula I:

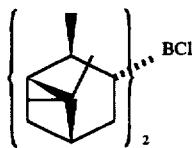

said ketone has the formula II:

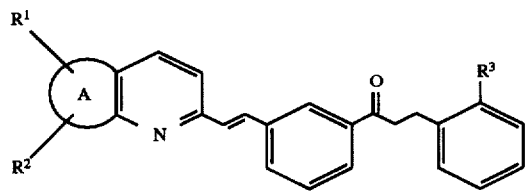

and said alcohol has the formula III:

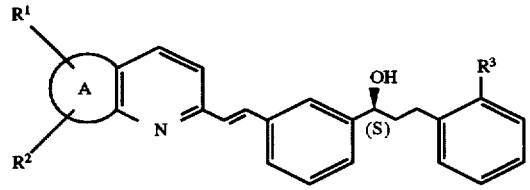

wherein

A is —CH=CH—S— or —CH=CH—CH=CH—;
$R^1$ and $R^2$ are independently hydrogen or a halogen;
$R^3$ is $CO_2R^6$, $COR^6$ or $C(R^7)_2$—O—$R^8$;
$R^6$ is hydrogen or lower alkyl;
$R^7$ is lower alkyl; and
$R^8$ is hydrogen or a hydroxy protecting group; and
said solvent is a polyoxygenated ether.

In a more preferred embodiment, $R^1$, $R^2$ and the bicyclic heterocycle to which they are attached together represent the moiety 7-chloroquinolinyl.

In the present process, step (a) is performed as previously described. The process of step (b) is preferably carried out in an ethereal solvent. For purposes of this specification, ethereal solvents include, but are not limited to ethers such as diethyl ether, di-n-butyl and diisopentyl ethers, anisole, cyclic ethers such as tetrahydropyran, 4-methyl-1,3-dioxane, dihydropyran, tetrahydrofuran, furan, 2-methyltetrahydrofuran and 2-ethoxytetrahydrofuran, most preferably tetrahydrofuran.

The reaction can be conducted at –25° to 25° C., preferably at about –20° to about 0° C. The reaction is allowed to proceed until essentially complete in about 1 to 100 hours; using the prochiral ketone and diisopinocampheylchloroborane of the preferred embodiment, the conversion to the optically active alcohol is typically 90% within about 3 hours at about –20° C.; and further conversion may be accelerated by allowing the reaction mixture to warm up to about 0° C. The reaction is preferably carried out at ambient pressure and under inert atmosphere, for example under nitrogen. After work-up, the desired optically active alcohol may be isolated by conventional methods, for example by crystallization, to provide the desired optical isomer of up to 99% enantiomeric excess.

Diisopinocampheylchloroborane is a valuable reagent for reducing prochiral ketones to the corresponding chiral hydroxy compounds. Compounds of formula III are illustrative of the utility of chiral hydroxy compounds. Compounds of formula III are intermediates in the preparation of leukotriene antagonists of formula IV:

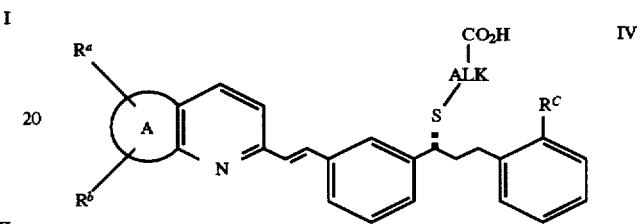

wherein A is as defined previously; $R^a$, $R^b$ are, inter alia, hydrogen or a halogen; and $R^c$ may be $CO_2R^d$, $COR^d$ or $C(R^e)_2$—OH; $R^d$ may be hydrogen or a lower alkyl, and $R^e$ may be lower alkyl; and ALK is for example cyclopropyl-1,1-(bis)methylene, isopropyl, and the like. Compounds of formula IV are useful as anti-asthmatic, anti-allergic, anti-inflammatory, and cytoprotective therapeutic agents. The preparation of these leukotriene antagonists using chiral hydroxy compounds of formula III are disclosed in U.S. Pat. No. 5,270,324 and EP Published Application 604114, as well as co-pending U.S. application Ser. No. 08/174,931. The afore-mentioned U.S. patent, EP application and co-pending U.S. application also disclose the preparation of the precursor prochiral ketones of formula II.

The following examples are provided to illustrate the present invention and are not intended to limit in any manner the scope of the invention which is solely defined by the claims of the application.

EXAMPLE 1

In Situ Preparation of Diisopinocampheylchloroborane $NaBH_4$ (1.89 g, 50.0 mmol) is charged to a 250 mL round-bottomed flask and the atmosphere is replaced with nitrogen. Dimethoxyethane (30 mL) and (+)α-pinene (85% ee, 31.8 mL, 200 mmol) are added and the mixture is cooled to –20° C. A solution of $BCl_3$ (55 mL, 1.0M in heptane, 55.0 mmol) is added at a rate such that the temperature of the reaction mixture does not exceed 0° C. (15 min). The mixture is aged at 0° C. for 15 min, room temperature for 1 hour, and 40° C. for 1 hour sequentially to give the chiral reducing agent diisopinocampheylchloroborane.

EXAMPLE 2

Reduction of Methyl 2-(3-(3-(2-(7-chloro-2quinolinyl) ethenyl)phenyl)-3-oxopropyl)benzoate to Methyl 2-(3-(3-(2-(7-chloro-2-quinolinyl)ethenyl)phenyl)-3(S)-hydroxypropyl)benzoate In a separate flask, a slurry of methyl 2-(3-(3-(2-(7-chloro-2-quinolinyl)ethenyl)phenyl)-3-oxopropyl)benzoate (hereinafter referred to as the ketoester, 25.77 g, 97.3 wt %, 55 mmol) in tetrahydofuran (200 mL) under nitrogen is prepared and then cooled to –20° C. The cooled slurry of the chiral reducing reagent from Example 1 (at −20° C.) is added to the ketoester, and the mixture is aged at −20° C. for hours, and then at 0° C. for 1 hour.

The reaction is quenched with benzaldehyde (15 mL) and the mixture is heated to 40° C. and aged for 1.5 h. After cooling to 20° C., it is slowly poured into a vigorously stirred aqueous $K_2CO_3$ (30 wt %, 100 ml). The stirring is continued until all the solid is dissolved. The organic layer is separated, filtered and then concentrated to ⅓ of its original volume (20–23 inches vacuum; 40°–50° C. bath temperature). Heptane (120 mL), followed by water (3 mL) is added to induce the crystallization. More heptane (120 mL) is then added and the mixture is aged at room temp. for 4 h to complete the crystallization. Filtration followed by washing the cake with THF/heptane (⅕, until the filtrate becomes almost colorless, 120 mL) and drying in a vacuum oven at 40° C. afforded 25.3 g of the title (S)-hydroxy ester monohydrate as a yellow solid (94.7% yield corrected for 98 wt % purity). The ee% is ≧99.0%.

What is claimed is:

1. A process for reducing a prochiral ketone to produce an optically active alcohol of high optical purity which comprises:
   (a) contacting sodium borohydride and boron trichloride with α-pinene having optical purity of about 70% or higher at a temperature of between about −40 and about 0° C., in a polyoxygenated ether solvent; and
   subsequently warming the reaction mixture to a temperature of between about 40° to about 60° C. to provide a composition containing diisopinocampheylchloroborane;
   (b) reacting a prochiral ketone with the composition obtained in (a) to provide the corresponding optically active alcohol of high optical purity.

2. A process of claim 1 wherein said α-pinene is (1R)(+) α-pinene, said diisopinocampheylchloroborane has the formula I:

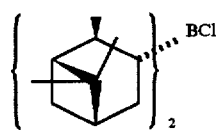

said ketone has the formula II:

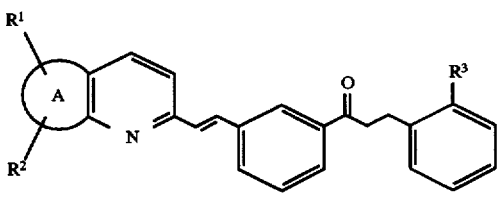

and said alcohol has the formula III:

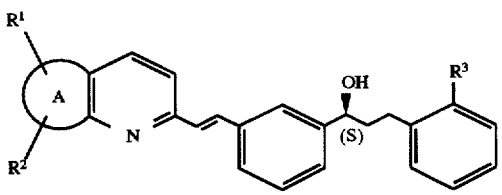

wherein

A is —CH=CH—S— or —CH=CH—CH=CH—;

$R^1$ and $R^2$ are independently hydrogen or a halogen;

$R^3$ is $CO_2R^6$; and $R^6$ is hydrogen or lower alkyl.

3. A process of claim 2 wherein $R^1$, $R^2$ and the bicyclic heterocycle to which they are attached together represent the moiety 7-chloroquinolinyl.

* * * * *